(12) United States Patent
Oh et al.

(10) Patent No.: US 6,613,323 B2
(45) Date of Patent: Sep. 2, 2003

(54) PLANT ESTERASES FOR PROTECTING PLANTS AND USES THEREOF

(75) Inventors: Boung-Jun Oh, Kwangju (KR); Young Soon Kim, Kwangju (KR); Moon Kyung Ko, Kwangju (KR); Hyun Hwa Lee, Kwangju (KR); Chae Eun Song, Kwangju (KR); Yong Hwan Lee, Kyunggi-Do (KR); Cheol-Yong Bae, Kyungsangnam-Do (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/735,660

(22) Filed: Dec. 14, 2000

(65) Prior Publication Data

US 2002/0110550 A1 Aug. 15, 2002

(51) Int. Cl.$^7$ .................................. A61K 38/46
(52) U.S. Cl. ..................... 424/94.6; 435/198; 504/117
(58) Field of Search ................. 424/94.6; 504/117; 435/198

(56) References Cited

U.S. PATENT DOCUMENTS

| | | | | |
|---|---|---|---|---|
| 6,018,038 A | * | 1/2000 | Oh | 436/23.6 |
| 6,080,565 A | * | 6/2000 | Koeller | 435/196 |
| 6,107,549 A | * | 8/2000 | Feng | 800/300 |

OTHER PUBLICATIONS

Jirage et al, PNAS, vol. 96, No. 23, "Arabidopsis thaliana PAD4 encodes a lipase–like . . . ", pp. 13583–13588, Nov. 9, 1999.
Falk et al, PNAS, vol. 96, "EDS1, an essential component of R gene–mediated disease . . . ", pp. 3292–3297, Mar. 1999.
Contreras et al, Journal of Biological Chemistry, vol. 271, No. 49, "Hormone–sensitive Lipase . . . ", pp. 31426–31430, Dec. 6, 1996.
Baudouin et al, Eur. J. Biochem, "Functional expression of a tobacco gene related to the serine . . . ", pp. 700–706, 1997.
Oh et al, J. Phytopathology, vol. 146, "A Microscopic Characterization of the Infection of . . . ", pp. 301–303, 1998.
Oh et al, J. Phytopathology, vol. 147, "Effect of Cuticular Wax Layers of Green and Red Pepper . . . ", pp. 547–552, 1999.

* cited by examiner

Primary Examiner—Irene Marx
(74) Attorney, Agent, or Firm—Jacobson Holman PLLC

(57) ABSTRACT

This invention relates to the use of enzymes for protection of plants against phytopathogenic fungi. In particular, the invention relates to the use of enzymes showing esterase activity for protecting plants against phytopathogenic fungi by inhibition of fungal appressorium formation. In addition, the invention relates to the use of recombinant pepper esterase expressed by using *Escherichia coli* to protect plants against phytopathogenic fungi by inhibition of fungal appressorium formation.

1 Claim, 6 Drawing Sheets

(1 of 6 Drawing Sheet(s) Filed in Color)

PLANT ESTERASES FOR PROTECTING PLANTS AND USES THEREOF

BACKGROUND OF THE INVENTION

This invention relates to the use of enzymes for protection of plants against phytopathogenic fungi. In particular, the invention relates to the use of enzymes showing esterase activity for protecting plants against phytopathogenic fungi by inhibition of fungal appressorium formation. In addition, the invention relates to the use of recombinant pepper esterase expressed by using *Escherichia coli* to protect plants against phytopathogenic fungi by inhibition of fungal appressorium formation.

Carboxylesterases are enzymes that catalyze the hydrolysis of compounds containing an ester bond. Genes encoding esterase or lipase enzymes have mainly been studied in mammals and microbes (Contreras et al. 1996; Feller et al. 1991; Kok et al. 1993; Langin et al. 1993; Osterund et al. 1997). Lipases in plants have been largely studied in germinating oil seeds where they provide energy for embryonic growth (Huang, 1987).

In plant-microbe interactions, a tobacco esterase gene, hsr203J, has been isolated from tobacco in a hypersensitive reaction against the pathogenic bacterium *Ralstonia solanacearum* (Badounin et al. 1997; Pontier et al. 1994). Recently, the EDS1 gene that is an essential component of the R gene-mediated disease resistance in Arabidopsis has been isolated and found to share homology with eukaryotic lipases (Falk et al. 1999). In addition, Arabidopsis PAD4, a gene required for expression of multiple defense responses after pathogen infection, encodes a lipase containing a lipase motif and the putative lipase catalytic triad (Jirage et al. 1999). However, the physiological roles of these enzymes in plant defense mechanisms remain unclear.

*Colletotrichum gloeosporioides* (Penz.) Penz. & Sacc. in Penz. is the causal agent of anthracnose diseases affecting fruit crops (Daykin 1984; Oh et al. 1998). The initial infection sequence of *C. gloeosporioides* consists of conidium germination and appressorium formation (Bailey et al. 1992). After that, the infection hypha is produced from the appressorium and penetrate into the host tissues to colonize the host. In the pepper-*C. gloeosporioides* pathosystem, only mature-unripe fruits showed susceptible interaction, while ripe fruits were resistant for interaction (Kim et al. 1999; Oh et al. 1998). A lower level of appressorium formation was observed in the resistant interaction in comparison to the susceptible interaction. This suggests that appressorium formation is positively linked to the development of anthracnose disease in this pathosystem.

The inventors previously cloned a pepper esterase gene (PepEST) that is highly expressed during the resistant interaction between the ripe fruit and *C. gloeosporioides* (U.S. Pat. No. 6,018,038; EP 1 018 554 A1). Here we have reported that recombinant PepEST protein expressed in *Escherichia coli* exhibited substrate specificity in hydrolyzing p-nitrophenyl esters. The recombinant PepEST inhibited appressorium formation of the anthracnose fungus in a dose-dependent manner, and protected pepper fruits against *C. gloeosporioides* infection. Finally, we propose that the recombinant PepEST affects a signal transduction pathway (s) involved in appressorium formation based on experimental results obtained with the rice blast fungus *Magnaporthe grisea*.

SUMMARY OF THE INVENTION

This invention provides for a use of enzymes showing esterase activity for protection of plants against phytopathogenic fungi. Preferentially, the enzymes are esterase that can protect plants against phytopathogenic fungi by inhibition of fungal appressorium formation. The use of the esterases that can be from animals and plants can be provided for the purpose of plant protection. More preferably, the esterase is from the genus Solanum of the family Solanaceae. The esterase can be, for example, from a pepper plant. The fungi can be, for instance, pepper anthracnose fungus *Colletotrichum gloeosporioides* and rice blast fungus *Magnaporthe grisea*.

A pepper esterase gene (PepEST) that is highly expressed during a resistant interaction between pepper (*Capsicum annuum*) and the anthracnose fungus *Colletotrichum gloeosporioides* has been previously cloned [The sequence of pepper esterase gene (PepEST) was disclosed in U.S. Pat. No. 6,018,038]. Glutathione-S-transferase tagged recombinant PepEST protein expressed in *Escherichia coli* showed substrate specificity for p-nitrophenyl esters [The sequence of pepper esterase protein (PepEST protein) was disclosed in U.S. Pat. No. 6,018,038].

Inoculation of susceptible-unripe pepper fruits with *C. gloeosporioides* spores amended with the recombinant PepEST protein did not cause anthracnose symptoms on the fruit. The recombinant protein has no fungicidal activity, but it significantly inhibits appressorium formation of the anthracnose fungus in a dose-dependent manner. An esterase from porcine liver also inhibited appressorium formation.

In addition, the recombinant PepEST protein inhibited appressorium formation in the rice blast fungus *Magnaporthe grisea*. Inhibition of appressorium formation in *M. grisea* by the recombinant protein was reversible by treatment with cAMP or 1,16-hexadecanediol. The results suggest that the recombinant protein regulates appressorium formation by modulating the cAMP-dependent signaling pathway in this fungus. Taken together, the PepEST esterase activity can inhibit appressorium formation of *C. gloeosporioides*, which may result in protection of the unripe fruit against the fungus

BRIEF DESCRIPTION OF THE DRAWINGS

The file of this patent contains at least one drawing executed in color.

DETAILED DESCRIPTION OF THE INVENTION

This invention provides for the use of enzymes for protection of plants against phytopathogenic fungi. In particular, the invention provides the use of a pepper esterase enzyme and a porcine esterase enzyme showing esterase activity for protecting plants against phytopathogenic fungi by inhibition of fungal appressorium formation. In addition, the invention provides the use of recombinant pepper esterase expressed by using *Escherichia coli* to protect plants against phytopathogenic fungi by inhibition of fungal appressorium formation.

Figure 1:
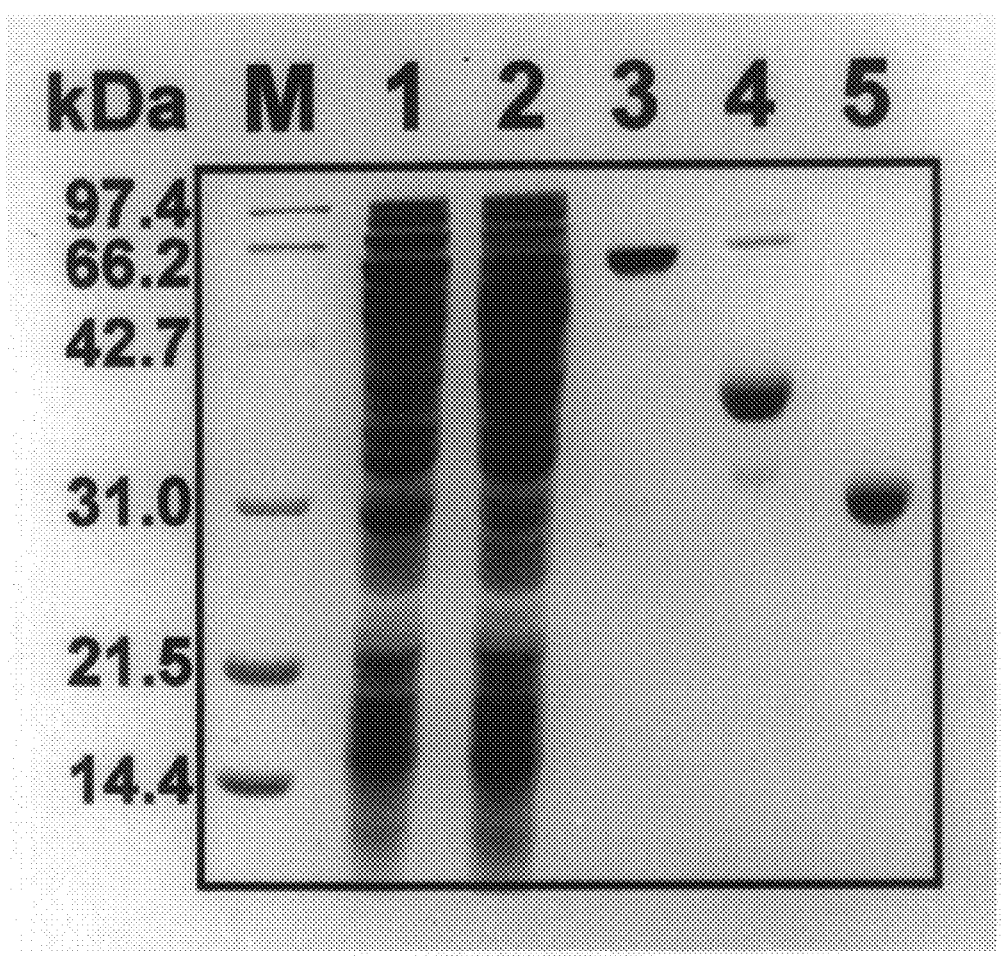
FIG. 1. SDS-PAGE analysis of the fusion protein produced in *Escherichia coli* at different step of purification. Protein molecular weight markers (lane M). Soluble faction of *E. coli* BL21 cells transformed pGEX-6P-1 plasmid that codes for GST-PepEST protein by IPTG induction (lane 1) and non-IPTG induction (lane 2). GST-PepEST fusion protein eluted from matrix by reduced glutathoine (lane 3). PepEST protein of supernatant fraction after PreScission Protease digestion (lane 4). Purified GST (lane 5).
Figure 2:
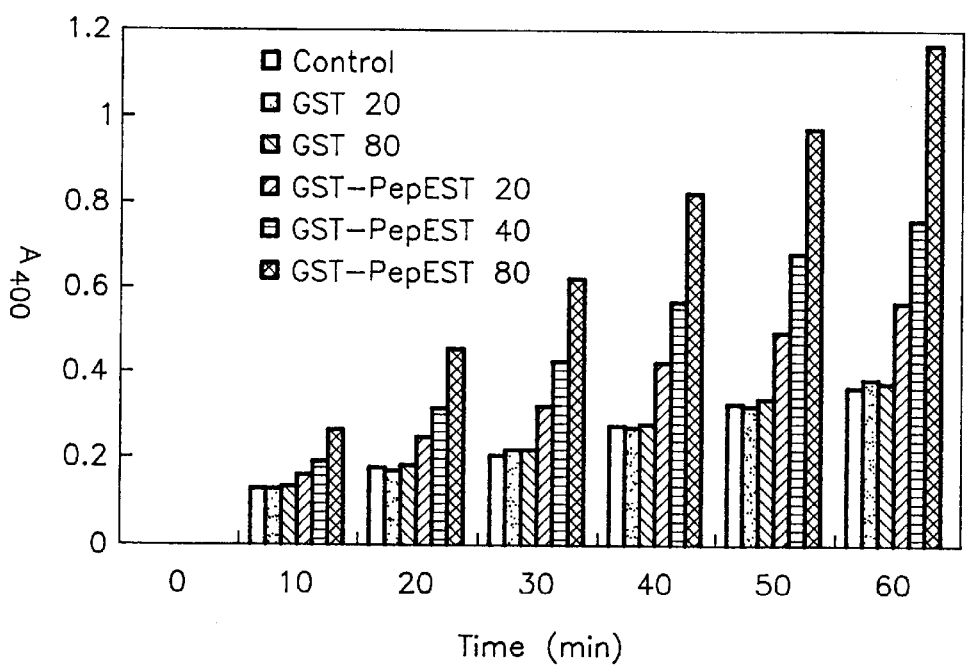
FIG. 2. Time-course and dose-dependence of esterase activity of the PepEST protein produced in *E. coli*. The GST-PepEST and GST protein was induced by *Escherichia coli* BL cells transformed with pGEX-6P-1 containing the PepEST sequence and with the vector alone, respectively, and purified by GST-glutathione affinity system. Enzymatic assay was performed with 1 mM p-nitrophenylbutyrate in the presence of various amount of the purified protein (Control: no protein, GST: 20 and 80 µg, and PepEST: 20, 40, and 80 µg).
Figure 3:
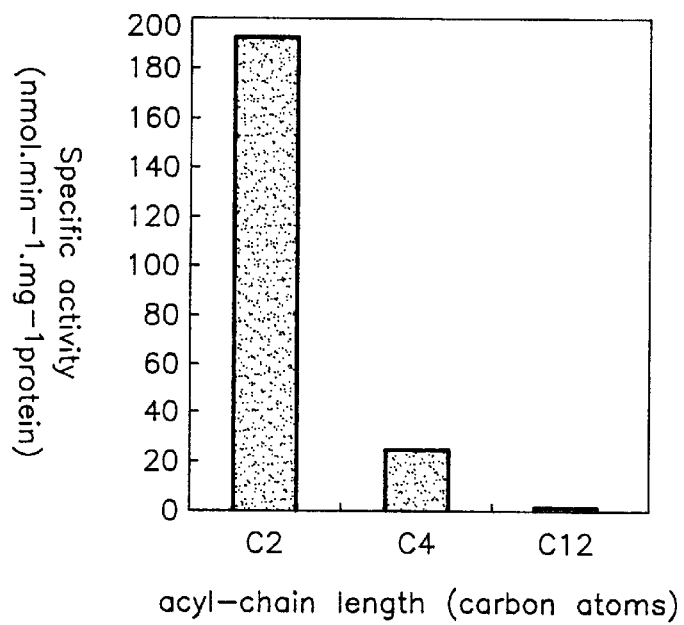
FIG. 3. Acyl-chain length specificity of the recombinant PepEST protein produced in *Escherichia coli*. Enzymatic assays were performed using p-nitrophenyl acetate ($C_2$),-butyrate ($C_4$), and -laurate ($C_{12}$) as substrates.

GST-tagged recombinant PepEST was produced in *E. coli* and purified to near homogeneity (FIG. 1). The recombinant protein was capable of hydrolyzing p-nitrophenyl esters used as substrate for carboxylesterase activity, while the GST protein could not degrade these substrates (FIG. 2). Using p-nitrophenyl esters, we examined the enzymatic activities according to acyl chain length. The enzyme activities of the recombinant protein were 192 nmol min$^{-1}$ mg$^{-1}$ for p-nitrophenylacetate ($C_2$), 24 nmol min$^{-1}$ mg$^{-1}$ for -butyrate ($C_4$), and 0.1 nmol min$^{-1}$ mg$^{-1}$ for -laurate ($C_{12}$) (FIG. 3). The activity was maximal for p-nitrophenylacetate, decreased 10-fold for -butyrate, and was much lower for -laurate.

Figure 4:
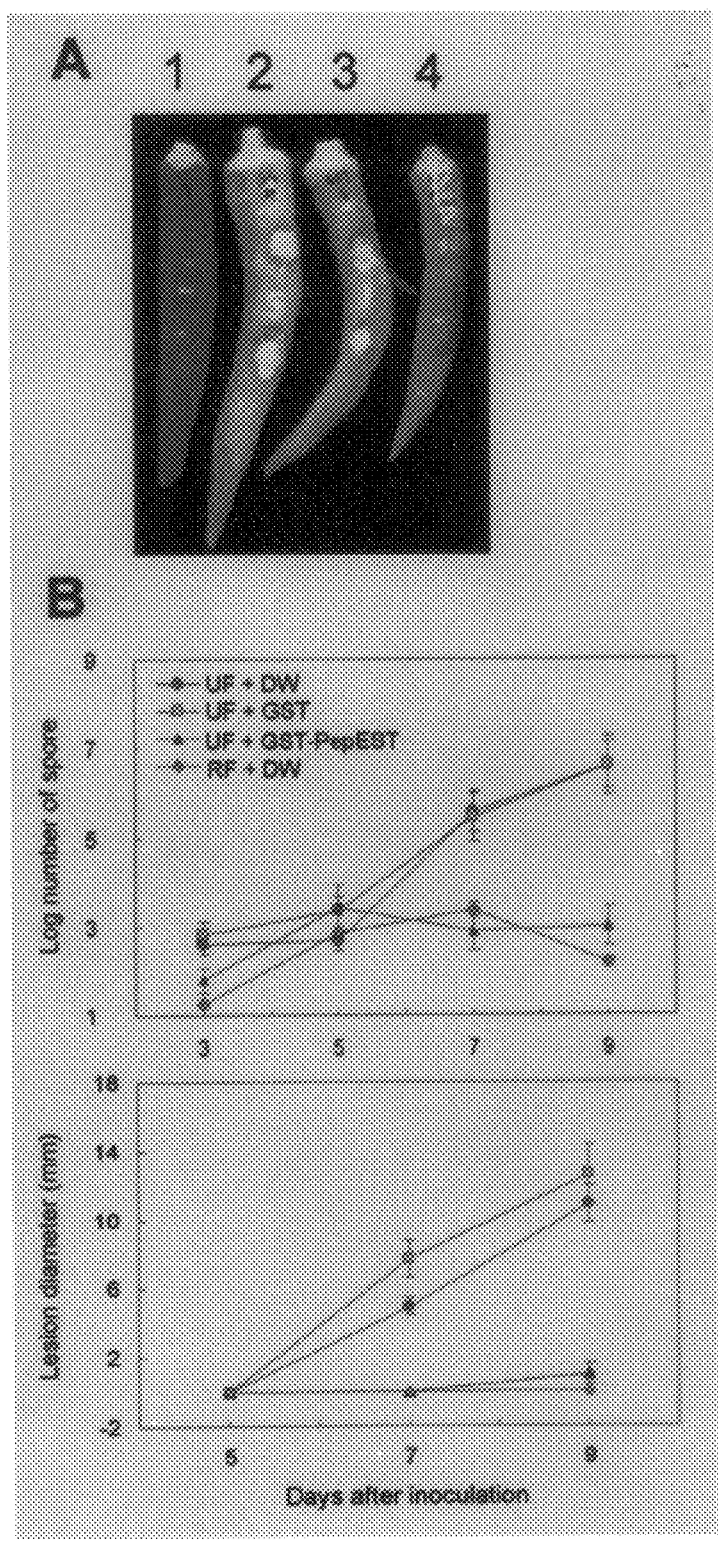
FIG. 4. Protection of the unripe fruit of pepper against *Colletotrichum gloeosporioides* infection by the recombinant PepEST. (A) Anthracnose symptoms on the pepper fruits observed 9 days after inoculation. The incompatible-ripe fruit inoculated with the fungus produced no disease symptoms (1). The compatible-unripe fruit treated with the fungus amended with 10 µl of sterile water (2) or 100 µg ml$^{-1}$ of GST protein (3) showed typical anthracnose symptoms. No apparent symptoms developed on unripe fruit treated with the fungus amended with 100 µg ml$^{-1}$ of GST-PepEST protein (4). (B) Anthracnose lesion diameter and number of spore were measured on both the unripe (UF) and ripe fruit (RF) infected with the fungus amended with 10 µl of sterile water (DW), 100 µg ml$^{-1}$ of GST, and 100 µg ml$^{-1}$ of GST-PepEST. Ripe fruit inoculated with the fungus was used as the control for resistant interaction. Lesion diameter and number of spore were measured at 3, 5, 7, and 9 days after inoculation. Each value for lesion diameter and number of spore represents the mean±standard error of 60 and 15 replicates, respectively.

It has been reported that inoculation of beans with the phytopathogenic fungus *Rhizoctonia solani* amended with fungal cutinases or esterases did not cause web blight symptoms (Parker and Köller 1998). We therefore tested whether the PepEST protein had the ability to prevent anthracnose disease symptoms on pepper fruits caused by *C. gloeosporioides*. Spore suspensions were drop-inoculated on both unripe and ripe fruits of pepper. Typical anthracnose symptoms with necrotic sunken lesions were observed on the unripe fruit within 5 days after inoculation, as we had previously observed (Oh et al. 1998) (FIG. 4A). However, spores amended with 100 µg ml$^{-1}$ of the recombinant protein were incompatible with the unripe fruits (FIG. 4B). The incompatible-ripe fruit used as positive control showed no anthracnose symptoms (Kim et al. 1999). Treatment of fruits with the recombinant protein alone did not cause any macroscopic changes (data not shown), while application of a spore suspension amended with 100 µg ml$^{-1}$ of GST protein did produce disease symptoms on the unripe fruit.

To further elucidate the protective activity of the recombinant PepEST described above, we investigated whether the recombinant protein had a direct effect on fungal growth in vitro. Spores of *C. gloeosporioides* were germinated on cover glasses in the presence of 100 µg ml$^{-1}$ of recombinant PepEST protein, GST, porcine esterase, or sterile water. Neither the recombinant protein nor GST or the porcine esterase had any fungicidal effect. The spores amended with water germinated at a rate of 63% (number of germinated spores/total number of spores observed×100) after 3 h incubation and 92% after 9 h of incubation (FIG. 5A) (Kim et al. 1999). Afterwards, the germination rate increased only slightly and was maintained up to 24 h of incubation. Spores amended with the recombinant protein germinated at a rate of 45% after 3 h incubation and 75% after 24 h incubation. GST or the porcine esterase also caused a reduction in the germination rate. However, the reduction of the germination rate in the presence of GST or the porcine esterase was less than that observed with the recombinant PepEST protein.

Figure 5:
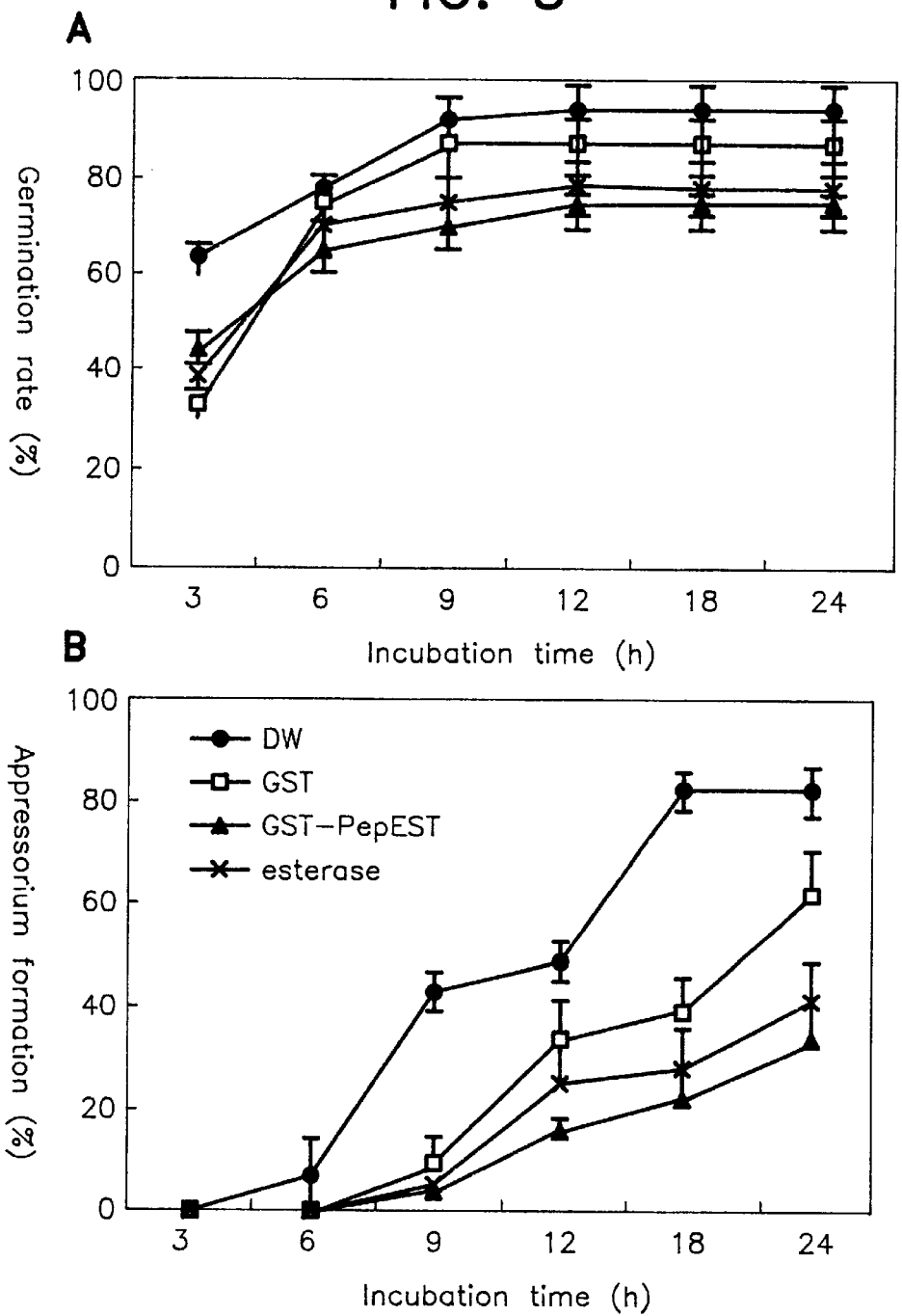
FIG. 5. Effect of the recombinant PepEST on spore germination and appressorium formation in *Colletotrichum gloeosporioides*. Spores amended with 10 µl of sterile water (DW), 100 µg ml$^{-1}$ of GST, 100 µg ml$^{-1}$ of GST/PepEST, or 100 µg ml$^{-1}$ of esterase were observed to evaluate (A) spore germination and (B) appressorium formation on cover glasses. At least 100 spores were counted per replicate. Each value represents the mean±standard error of 9 replicates.
Figure 6:
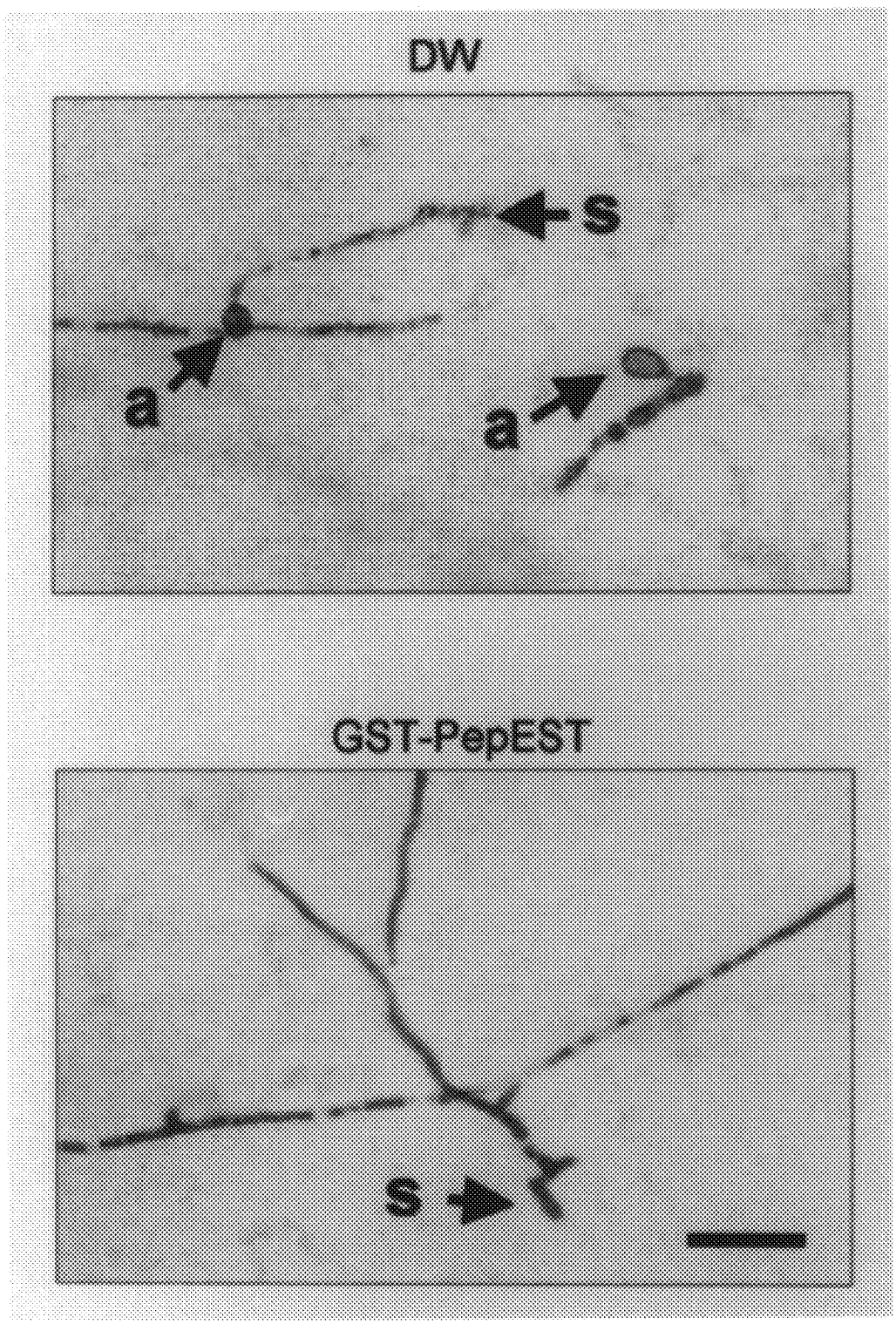
FIG. 6. Inhibition of appressorium formation in *Colletotrichum gloeosporioides* amended with 10 µl of the recombinant protein (100 µg ml$^{-1}$) on cover glasses. A spore suspension with sterile water (DW) was used as the control. The fungus treated with the recombinant protein exhibited mycelial growth without appressorium formation (GST-PepEST). The fungus was stained with 0.1% (w/v) cotton blue in lactophenol 24 h after inoculation. Bar represents 25 µm. a: appressorium, s: spore.

We then examined the effect of the recombinant PepEST on appressorium formation. Appressorium formation of *C. gloeosporioides* amended with sterile water was observed after 3 h of incubation (FIG. 5B). After 24 h, the appressorium formation rate had increased to 82% (the number of spore with appressorium/total number of spores observed× 100). *C. gloeosporioides* amended with the recombinant protein did not form an appressorium before 6 h of incubation. Maximal appressorium formation by the fungus in the presence of the recombinant protein was 34% after 24 h of incubation. In particular, the fungus treated with the recombinant protein exhibited mycelial growth, but without appressorium formation (FIG. 6). The appressorium formation after 24 h of incubation in the presence of GST or the liver esterase was 62% and 41%, respectively.

Figure 7:
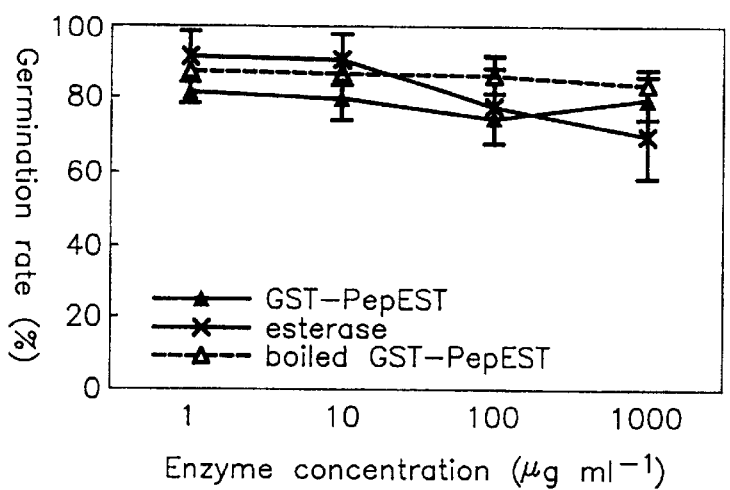
FIG. 7. Effect of recombinant PepEST concentration on (A) spore germination and (B) appressorium formation of *Colletotrichum gloeosporioides* in vitro. A boiled GST-PepEST was used as a negative control. Spore suspensions were amended with 10 µl of the recombinant protein, the boiled recombinant protein or esterase to the final concentrations of 1, 10, 100, and 1,000 µg ml$^{-1}$. At least 100 spores were counted per replicate. Each value represents the mean±standard error of 9 replicates. (C) Comparison of hydrolyzing activity of the recombinant PepEST (1 µg), the boiled recombinant PepEST (1 µg), and the esterase (10 ng) on p-nitrophenylbutyrate.
Figure 7:
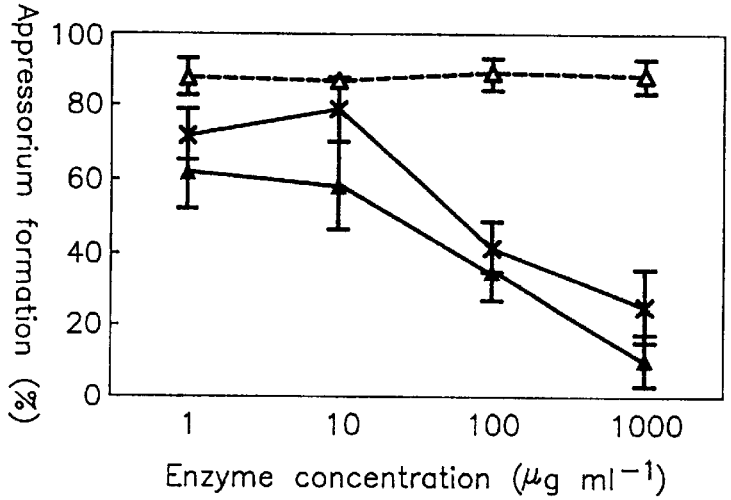
Figure 7:
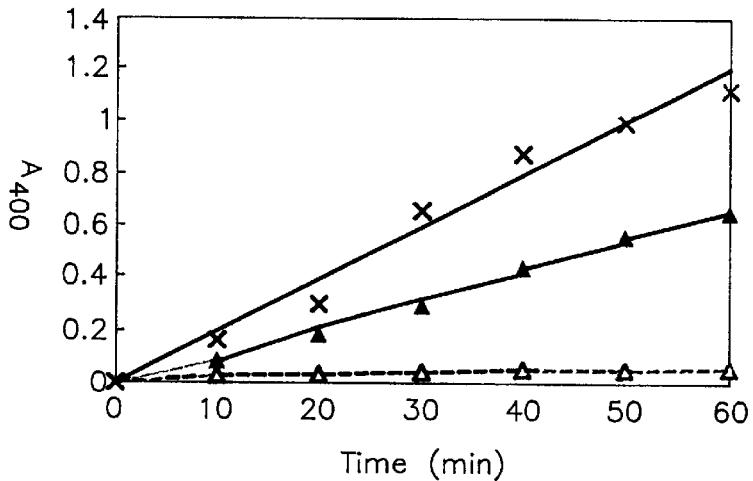

We then examined the dose dependency of the inhibition of spore germination and appressorium formation by the recombinant PepEST. The fungal spores were amended with 1, 10, 100, and 1,000 µg ml$^{-1}$ of recombinant PepEST protein or porcine esterase. One-hundred microgram ml$^{-1}$ of the recombinant protein inhibited spore germination only slightly, while 1,000 µg ml$^{-1}$ did not produce an inhibition at all. This indicates that the recombinant protein had no significant effect on spore germination (FIG. 7A). However, the porcine esterase did inhibit spore germination in the dose-dependent manner. Both the recombinant protein and the porcine esterase significantly inhibited appressorium formation in a dose-dependent manner (FIG. 7B). We also compared the hydrolyzing activity of the recombinant PepEST to that of the porcine esterase using p-nitrophenylbutyrate in vitro (FIG. 7C). The hydrolyzing activity of the esterase (10 ng) was much higher than that of the recombinant protein (1 μg). A boiled GST-PepEST fusion protein did not affect the inhibition of spore germination and appressorium formation, and did not hydrolyze p-nitrophenylbutyrate.

We next studied the effect of recombinant PepEST on appressorium formation of M. grisea. Spore suspensions of M. grisea amended with a series of dilutions of the recombinant protein were incubated on the hydrophobic surface of GelBond film for 24 h. The recombinant protein at 10 μg ml$^{-1}$ significantly inhibited appressorium formation (Table 1). Greater dilutions of the recombinant protein gradually lost their inhibitory capacity in a dose-dependent manner. The recombinant protein at the concentrations of 0.625 and 0.3125 $\mu$g ml$^{-1}$ did not have any significant inhibitory effect on the appressorium formation in *M. grisea*.

As a first step to dissect the mechanism(s) of the inhibition, we looked for an effect of the recombinant PepEST protein on signal transduction pathways involved in appressorium formation. The inhibition of appressorium formation on the hydrophobic surface of GelBond by the recombinant protein was reversible by treating of the spores with cAMP or 1,16-hexadecanediol. The appressoria induced by cAMP or 1,16-hexadecanediol in the presence of recombinant PepEST protein were well melanized and indistinguishable from those formed in the untreated control. 1,16-hexadecanediol was much more effective than cAMP in inducing appressorium formation.

EXAMPLES

Protein Expression and Enzymatic Study

The open reading frame of PepEST cDNA (GenBank accession number AF122821, U.S. Pat. No. 6,018,038) was amplified by PCR and inserted in-frame with the glutathione-S-transferase (GST) coding sequence in the expression vector pGEX-6p-1 (Pharmacia, Sweden) between an EcoRI and an XhoI site. *E. coli* BL21 was transformed with the resulting plasmid and induced to produce the GST-PepEST fusion protein by isopropylthio-B-D-galactoside (IPTG). The bacterial cells were then suspended in PBS buffer and lysed by sonication. Collected supernatants were mixed with the Glutathione Sepharose 4B matrix and incubated with gentle agitation at room temperature for 30 min. The matrix was washed three times with PBS, and the protein bound to the matrix was eluted using 10 mM reduced glutathione in 50 mM Tris-HCl (pH 8.0). The GST-PepEST fusion protein was expressed and purified according to the manufacturer's instructions. Protein content was determined following the Bradford procedure (1979).

Esterase activity was measured as the rate of hydrolysis of p-nitrophenyl esters that were determined spectrophotometrically at 400 nm in a Beckmann spectrophotometer (Heymann et al. 1981). The esterase activity was measured at 30° C. in a reaction mixture consisting of 0.2 ml of 0.5 M HEPES pH 8.0, 1.8 ml of 1 mM p-nitrophenyl esters, and 20 $\mu$g of the recombinant PepEST. The specific activity in relation to the acyl chain length was measured using p-nitrophenyl acetate ($C_2$), -butyrate ($C_4$), and -laurate ($C_{12}$). All measurements were corrected for non-enzymatic hydrolysis of p-nitrophenyl esters.

Fungal Inoculum and Plant Material

A monoconidial isolate of *C. gloeosporioides* was cultured on potato dextrose agar (Difco, Detriot, Mich.) for 5 days in the dark at 28° C. Conidia were harvested and suspended in sterile distilled water. Ten microliter of spore suspension (5×10$^5$ spores/ml) was used in drop inoculations in vitro and in vivo.

*M. grisea* 70-15 was kindly provided by Dr. E. Ellingboe at the University of Wisconsin, Wis. Fungal cultures were grown on oatmeal agar (50 g oatmeal per liter) at 22° C. under fluorescent light to promote conidiation. Conidia were collected from 10-day-oldcultures and washed twice with distilled water.

Unripe mature-green and ripe red fruits of pepper cv. Nokkwang were raised under greenhouse condition (Oh et al. 1998).

*C. gloeosporioides* Spores Amended with Recombinant PepEST Protein

Ten microliter aliquots of spore suspension (5×10$^5$ spores/ml) were amended with 10 $\mu$l (to a final concentration of 100 $\mu$g ml$^{-1}$) of recombinant PepEST, GST, porcine esterase (commercially sold by SIGMA, USA), or sterile water (as the control) and applied to cover glasses in the form of drops. The cover glasses were incubated in humidified chambers at 25° C. in the dark for 24 h. Then, the fungus on the cover glasses was stained with 0.1% (w/v) cotton blue in lactophenol. Spore germination and appressorium formation on the cover glasses was observed through a microscope (Kim et al., 1999). Dosage/effect experiments for the recombinant protein and the esterase on fungal morphogenesis were performed by the same procedure. Inoculation tests using spores amended with 100 $\mu$g ml$^{-1}$ of the recombinant PepEST or GST were performed on healthy unripe and ripe fruits as previously described (Oh et al., 1998).

*M. grisea* Spores Amended with Recombinant PepEST Protein

Appressorium formation was measured on GelBond film (FMC BioProducts, Rockland, Me.) as previously described (Lee and Dean, 1993). Briefly, a 6 $\mu$l drop of a spore suspension (5×10$^5$ spores/ml) was placed on GelBond film, sealed in a moistened box, and incubated at 24° C. for 24 hours. The percentages of germinated and germinating spores forming appressoria were determined by direct microscopic examination of at least 100 spores per replicate in at least three experiments with three replicates per treatment. A series of dilutions of the recombinant PepEST (final concentrations: 10, 5, 2.5, 1.25, 0.625, and 0.3125 $\mu$g ml$^{-1}$) was added to the spore suspension. In the complementation assays, cAMP (10 mM) or 1,16-hexadecanediol (0.01 mM) was added to spore suspensions in the presence of the recombinant PepEST.

Esterase Activity and Substrate Specificity of Recombinant PepEST Protein

GST-tagged recombinant PepEST was produced in *E. coli* and purified to near homogeneity (FIG. 1). The recombinant protein was capable of hydrolyzing p-nitrophenyl esters used as substrate for carboxylesterase activity, while the GST protein could not degrade these substrates (FIG. 2). Using p-nitrophenyl esters, we examined the enzymatic activities according to acyl chain length. The enzyme activities of the recombinant protein were 192 nmol min$^{-1}$ mg$^{-1}$ for p-nitrophenylacetate ($C_2$), 24 nmol min$^{-1}$ $^{mg-1}$ for -butyrate ($C_4$), and 0.1 nmol min$^{-1}$ mg$^{-1}$ for -laurate ($C_{12}$) (FIG. 3). The activity was maximal for p-nitrophenylacetate, decreased 10-fold for -butyrate, and was much lower for -laurate.

Effect of Recombinant PepEST Protein on Symptom Development Upon *C. gloeosporioides* Infection It has been reported that inoculation of beans with the phytopathogenic fungus *Rhizoctonia solani* amended with fungal cutinases or esterases did not cause web blight symptoms (Parker and Köller 1998). We therefore tested whether the PepEST protein had the ability to prevent anthracnose disease symptoms on pepper fruits caused by *C. gloeosporioides.* Spore suspensions were drop-inoculated on both unripe and ripe fruits of pepper. Typical anthracnose symptoms with necrotic sunken lesions were observed on the unripe fruit within 5 days after inoculation, as we had previously observed (Oh et al. 1998) (FIG. 4A). However, spores amended with 100 $\mu$g ml$^{-1}$ of the recombinant protein were incompatible with the unripe fruits (FIG. 4B). The incompatible-ripe fruit used as positive control showed no anthracnose symptoms (Kim et al. 1999). Treatment of fruits with the recombinant protein alone did not cause any macroscopic changes (data not shown), while application of a spore suspension amended with 100 $\mu$g ml$^{-1}$ of GST protein did produce disease symptoms on the unripe fruit. Thus, our data suggest that the PepEST protein has an protective activity that prevented anthracnose disease development on unripe fruit infected with *C. gloeosporioides.*

Inhibition of Appressorium Formation by Recombinant PepEST Protein in vitro

To further elucidate the protective activity of the recombinant PepEST described above, we investigated whether the recombinant protein had a direct effect on fungal growth in vitro. Spores of *C. gloeosporioides* were germinated on cover glasses in the presence of 100 $\mu$g ml$^{-1}$ of recombinant PepEST protein, GST, porcine esterase, or sterile water. Neither the recombinant protein nor GST or the porcine esterase had any fungicidal effect. The spores amended with water germinated at a rate of 63% (number of germinated spores/total number of spores observed×100) after 3 h incubation and 92% after 9 h of incubation (FIG. 5A) (Kim et al. 1999). Afterwards, the germination rate increased only slightly and was maintained up to 24 h of incubation. Spores amended with the recombinant protein germinated at a rate of 45% after 3 h incubation and 75% after 24 h incubation. GST or the porcine esterase also caused a reduction in the germination rate. However, the reduction of the germination rate in the presence of GST or the porcine esterase was less than that observed with the recombinant PepEST protein.

We then examined the effect of the recombinant PepEST on appressorium formation. Appressorium formation of *C. gloeosporioides* amended with sterile water was observed after 3 h of incubation (FIG. 5B). After 24 h, the appressorium formation rate had increased to 82% (the number of spore with appressorium/total number of spores observed× 100). *C. gloeosporioides* amended with the recombinant protein did not form an appressorium before 6 h of incubation. Maximal appressorium formation by the fungus in the presence of the recombinant protein was 34% after 24 h of incubation. In particular, the fungus treated with the recombinant protein exhibited mycelial growth, but without appressorium formation (FIG. 6). The appressorium formation after 24 h of incubation in the presence of GST or the liver esterase was 62% and 41%, respectively. Taken together, these results indicate that the recombinant PepEST affects more significantly to appressorium formation than to spore germination.

We then examined the dose dependency of the inhibition of spore germination and appressorium formation by the recombinant PepEST. The fungal spores were amended with 1, 10, 100, and 1,000 $\mu$g ml$^{-1}$ of recombinant PepEST protein or porcine esterase. One-hundred microgram ml$^{-1}$ of the recombinant protein inhibited spore germination only slightly, while 1,000 $\mu$g ml$^{-1}$ did not produce an inhibition at all. This indicates that the recombinant protein had no significant effect on spore germination (FIG. 7A). However, the porcine esterase did inhibit spore germination in the dose-dependent manner. Both the recombinant protein and the porcine esterase significantly inhibited appressorium formation in a dose-dependent manner (FIG. 7B). We also compared the hydrolyzing activity of the recombinant PepEST to that of the porcine esterase using p-nitrophenylbutyrate in vitro (FIG. 7C). The hydrolyzing activity of the esterase (10 ng) was much higher than that of the recombinant protein (1 $\mu$g). A boiled GST-PepEST fusion protein did not affect the inhibition of spore germination and appressorium formation, and did not hydrolyze p-nitrophenylbutyrate.

Effect of Recombinant PepEST Protein on Appressorium Formation of *M. grisea*

We next studied the effect of recombinant PepEST on appressorium formation of *M. grisea.* Spore suspensions of *M. grisea* amended with a series of dilutions of the recombinant protein were incubated on the hydrophobic surface of GelBond film for 24 h. The recombinant protein at 10 $\mu$g ml$^{-1}$ significantly inhibited appressorium formation (Table 1). Greater dilutions of the recombinant protein gradually lost their inhibitory capacity in a dose-dependent manner. The recombinant protein at the concentrations of 0.625 and 0.3125 $\mu$g ml$^{-1}$ did not have any significant inhibitory effect on the appressorium formation in *M. grisea.*

As a first step to dissect the mechanism(s) of the inhibition, we looked for an effect of the recombinant PepEST protein on signal transduction pathways involved in appressorium formation. The inhibition of appressorium formation on the hydrophobic surface of Gelbond by the recombinant protein was reversible by treating of the spores with cAMP or 1,16-hexadecanediol. The appressoria induced by cAMP or 1,16-hexadecanediol in the presence of recombinant PepEST protein were well melanized and indistinguishable from those formed in the untreated control. 1,16-hexadecanediol was much more effective than cAMP in inducing appressorium formation.

TABLE 1

Effect of the recombinant PepEST on appressorium formation in *Magnaporthe grisea*

| Treatment | Appressorium formation (% ± standard error) |
|---|---|
| Water control | 76.2 ± 9.1 |
| Buffer control | 79.8 ± 10.4 |
| PepEST (10)[a] | 38.4 ± 5.9 |
| PepEST (5) | 46.1 ± 3.2 |
| PepEST (2.5) | 44.7 ± 3.3 |
| PepEST (1.25) | 54.3 ± 3.1 |
| PepEST (0.625) | 68.6 ± 6.8 |
| PepEST (0.3125) | 70.7 ± 11.1 |
| PepEST (10) + 10 mM cAMP | 70.4 ± 12.4 |
| PepEST (10) + 0.01 mM 1,16-hexadecanediol | 93.7 ± 1.6 |

[a]Recombinant PepEST at the concentration of $\mu$g ml$^{-1}$

Discussion

Genes (EDS1, hsr203J, and PAD4) encoding a lipase motif (GXSXG) and the putative catalytictriad in lipases composed of Ser, Asp, and His have been isolated from various plant tissues involved in plant-microbe interactions (Falk et al. 1999; Jirage et al. 1999; Pontier et al. 1994). We have cloned a pepper esterase gene (PepEST) that is highly expressed during an incompatible interaction between pepper fruit and *C. gloeosporioides*. Recombinant PepEST protein expressed in *E. coli* exhibited substrate specificity for p-nitrophenyl esters in vitro. The recombinant PepEST activity was maximal for p-nitrophenylacetate, decreased significantly for -butyrate, and was barely detectable for -laurate. These data indicate that the recombinant protein was active as a single polypeptide and most effective on short-chain acyl esters. The substrate specificity of the PepEST thus differed from that of HSR203J, a tobacco esterase that was as active on both p-nitrophenylacetate and -butyrate (Baudouin et al. 1997). Although both esterases exhibited somewhat different substrate specificities, they may still have similar natural substrates. This possibility is suggested by the fact that both esterases accumulate highly only during incompatible interactions. However, the exact physiological role for the esterases in plant defenses has not been determined yet.

Appressorium formation by many fungal pathogens is a prerequisite for the infection of a host plant (Staple and Hoch 1987). In a previous study (Kim et al. 1999), a lower level of appressorium formation had been observed on a resistant-ripe fruit in comparison to a compatible-unripe fruit of pepper. In this study we found that the recombinant PepEST could inhibit appressorium formation of *C. gloeosporioides* resulting in protection of the fruit from infection by the fungus. Higher concentrations of the recombinant PepEST protein and of the porcine esterase caused a significant reduction in appressorium formation. However, the boiled recombinant PepEST did not hydrolyze p-nitrophenylbutyrate and did not affect the inhibition of appressorium formation. The porcine esterase also protected the unripe fruit against fungal infection (data not shown), suggesting that the inhibition of appressorium formation was caused by the esterase activity of the recombinant PepEST.

The hydrolytic activity of the porcine esterase (10 ng) was similar to that of the recombinant PepEST (1 $\mu$g) (FIG. 7C). However, higher concentrations of the esterase (100 $\mu$g ml$^{-1}$) resulted in less inhibition of appressorium formation than that resultant of the recombinant protein (100 $\mu$g ml$^{-1}$) (FIG. 7B). This suggests that, although the recombinant protein exhibited lower hydrolyzing activity on p-nitrophenylbutyrate, the PepEST protein seems to have a specific activity that can strongly inhibit appressorium formation of the fungus.

Many phytopathogenic fungi secrete cutinases that act as esterases breaking the ester linkages between cutin molecules of plant cuticles in order to invade plants (Kolattukudy 1985; Köller et al. 1982). Fungal cutinases have a lipase motif (GXSXG) and a catalytic triad composed of Ser, Asp, and His (Sweigard et al. 1992). It is interesting that esterases are used on both sides of the plant-microbe interaction. It has been hypothesized that another role for cutinases may be the induction of disease resistance in plants via the generation of cutin monomers from plant cuticles (Schweizer et al. 1996a,b). Exogenous application of the PepEST to the unripe fruit induced the generation of $H_2O_2$ and the expression of defense related genes (Ko and Oh, unpublished results). These results suggest that PepEST may have the ability to affect fungal morphogenesis as well as to induce defense responses similar to the fungal cutinases.

The inhibition of appressorium formation in *M. grisea* suggests that PepEST may also have an inhibitory potential against fungi other than the anthracnose fungus. Furthermore, treatment with cAMP or 1,16-hexadecanediol restored the appressorium formation in *M. grisea* inhibited by PepEST. This suggests that the inhibitory mechanism exhibited by PepEST may operate upstream of the sites of action of cAMP or 1,16-hexadecanediol. A similar phenomenon has been observed for these effector chemicals and polyamines before (Choi et al. 1998). It is likely that PepEST may decrease intracellular cAMP levels or directly or indirectly increase the requirement for cAMP. Although the precise mechanisms involved in the inhibition of the appressorium formation by PepEST are not yet clear, our data suggest that PepEST exerts its effect by modulating the cAMP and 1,16-hexadecanediol signal transduction pathway.

REFERENCES

Bailey, J. A., O'Connell, R. J., Pring, R. J., and Nash, C. 1992. Infection strategies of Colletotrichum species. In Colletotrichum: Biology, Pathology and Control (Bailey J. A. and Jeger, J. A., eds). UK: CAB International, pp. 88–120.

Baudouin, E., Charpenteau, M., Roby, D., Marco, Y., Ranjeva, R., and Ranty, B. 1997. Functional expression of a tobacco gene related to the serine hydrolase family. Esterase activity towards short-chain dinitrophenyl acylesters. Eur. J. Biochem. 248:700–706.

Bradford, M. M. 1976. A rapid and sensitive method for the quantitation of microgram quantities of protein utilizing the principle of protein-dye binding. Anal. Biochem. 72:248–254.

Choi, W. B., Kang, S. H., Lee, Y. W., and Lee, Y. H. 1998. Cyclic AMP restores appressorium formation inhibited by polyamines in *Magnaporthe grisea*. Phytopathology 88:58–62.

Contreras, J. A., Karlsson, M., Osterlund, T., Laurell, H., Svensson, A., and Holm, C. 1996. Hormone-sensitive lipase is structurally related to acetylcholinesterase, bile salt-stimulated lipase, and several fungal lipases. J. Biol. Chem. 271:31426–31430.

Daykin, M. E. 1984. Infection in blueberry fruit by *Colletotrichum gloeosporioides*. Plant Dis. 68:984–950.

Falk, A., Feys, B. J., Frost, L. F., Jones, J. D. G., Daniels, M. J., and Parker, J. E. 1999. EDS1, an essential component of R gene-mediated disease resistance in Arabidopsis has homology to eukaryotic lipases. Proc. Natl. Acad. Sci. USA 96:3292–3297.

Fauth, M., Schweizer, P., Buchala, A., Markstadter, C., Riederer, M., Kato, T., and Kauss, H. 1998. Cutin monomers and surface wax constitutes elicit $H_2O_2$ in conditioned cucumber hypocotyl segments and enhance the activity of other $H_2O_2$ elicitors. Plant Physiol. 117:1373–1380.

Feller, G., Thirty, M., and Gerday, C. 1991. Nucleotide sequence of the lipase gene lip2 from the antarctic psychrotroph Moraxella TA144 and site-specific mutagenesis of the conserved serine and histidine residues. DNA Cell Biol. 10:381–388.

Heymann, E., Mentlein, R., and Rix, H. 1981. Hydrolysis of aromatic amide as assay for carboxylesterases-amides. Methods Enzymol. 77:333–344.

Huang, A. H. C. 1987. Lipases. In *The biochemistry of plants* (Stumpf, P. K. and Conn, E. E., eds) vol. 9. Academic Press. Inc. pp. 91–119.

Jirage, D., Tootle, T. L., Reuber, T. L., Frost, L. N., eyes, B. J., Parker, J. E., Ausubel, F. M., and Glazebrook, J. 1999. *Arabidopsis thaliana* PAD4 ncodes a lipase-like gene that is important for salicylic acid signaling. Proc. Natl. Acad. Sci. USA 96:13583–13588.

Kim, K. D., Oh, B. J., and Yang, J. 1999. Differential interactions of a *Colletotrichum gloeosporioides* isolate with green and red pepper fruits. Phytoparasitica 27:97–106.

Kok, R. G., Christoffels, V. M., Volsman, B., and Hellingwerf, K. J. 1993. Growth-phase-dependent expression of the lipolytic system of *Acinetobacter calcoaceticus* BD413: cloning of a gene coding one of the esterases. J. Gen. Microbiol. 139:2329–2342.

Kolattukudy, P. E. 1985. Enzymatic penetration of the plant cuticle by fungal pathogens. Annu. Rev. Phytopathol. 23:223–250.

Kolattukudy, P. E., Rogers, L. M., Li, D., Hwang, C.-S., and Flaishman, M. A. 1995. Surface signaling in pathogenesis. Proc. Natl. Acad. Sci. USA 92:4080–4087.

Köller, W., Allan, C. R., and Kolattukudy, P. E. 1982. Role of cutinase and cell wall degrading enzymes in infections of *Pisum sativum* by *Fusarium soloni* f. sp. *pisi*. Physiol. Plant Pathol. 20:47–60.

Langin, D., Laurell, H., Stenson-Holst, L., Belfrage, P., and Holm, C. 1993. Gene organization and primary structure of human hormone-sensitive lipase: possible significance of a sequence homology with a lipase of Moraxella TA144, an antarctic bacterium. Proc. Natl. Acad. Aci. USA 90:4897–4901.

Lee, Y. H., and Dean, R. A. 1993. cAMP regulates infection structure formation in the plant pathogenic fungus *Magnaporthe grisea*. Plant Cell 5:693–700.

Oh, B. J., Kim, K. D., and Kim, Y. S. 1998. A microscopic characterization of the infection of green and red pepper fruits by an isolate of *Colletotrichum gloeosporioides*. J. Phytopathol. 146:301–303.

Osterlund, T., Contreras, J. A., and Holms, C. 1997. Identification of essential aspartic acid and histidine residues of hormone-sensitive lipase: apparent residues of the catalytic triad. FEBS Lett. 403:259–262.

Parker, D. M., and Köller, W. 1998. Cutinase and other lipolytic esterases protect bean leaves from infection by *Rhizoctonia solani*. Mol. Plant-Microbe Interac. 11:514–522.

Pontier, D., Godlard, L., Marco, Y., and Roby, D. 1994. hsr203J, a tobacco gene whose activation is rapid, highly localized and specific for incompatible plant/pathogen interactions. Plant J. 5:507–521.

Schweizer, P., Felix, G., Buchala, A., Müller, C., and Métraux, J.-P. 1996a. Perception of free cutin monomers by plant cells. Plant J. 10:331–341.

Schweizer, P., Jeanguenat, A., Whitacre, D., and Métraux, J.-P. 1996b. Induction of resistance in barley against *Erysiphe graminis* f. sp. *hordei* by free cutin monomers. Physiol. Mol. Plant Pathol. 49:103–120.

Staple, R. C., and Hoch, C. H. 1987. Infection structures: form and function. Exp. Mycol. 11:163–169.

Sweigard, J. A., Chumley, F. G., and Valent, B. 1992. Cloning and analysis of CUT1, a cutinase gene from *Magnaporthe grisea*. Mol. Gen. Genet. 232:174–182.

Thordal-Christensen, H., Zhang, Z., Wei, Y., and Collinge, D. B. 1997. Subcellular localization of $H_2O_2$ in plants: $H_2O_2$ accumulation in papillae and hypersensitive response during the barley-powdery mildew interaction. Plant J. 11:1187–1194.

Woloshuk, C. P., and Kolattukudy, P. E. 1986. Mechanisms by which contact with plant cuticle triggers cutinase gene expression in the spores of *Fusarium solani* f. sp. *pisi*. Proc. Natl. Acad. Sci. USA 83:1704–1708.

What is claimed is:

1. A method of protecting a plant from fungal infection by administering a pepper esterare (PepEST) in an effective dose with a concentration of about 10 to 1,000 mg/ml to the plant wherein the pepper esterase protects the plant from *Colletotrichum gloeosporioides* or *Magnaprothe grisea* by inhibiting fungal appressorium formation.

* * * * *